(12) United States Patent
Kiener et al.

(10) Patent No.: US 6,214,604 B1
(45) Date of Patent: Apr. 10, 2001

(54) BIOTECHNICAL PRODUCTION PROCESS OF PIPERAZINE R-α-CARBOXYLIC ACIDS AND PIPERAZINE S-α-CARBOXYLIC ACID AMIDE

(75) Inventors: Andreas Kiener, Visp; Jean-Paul Roduit, Grône; Klaus Heinzmann, Visperterminen, all of (CH)

(73) Assignee: Lonza AG, Basel (CH)

( * ) Notice: Subject to any disclaimer, the term of this patent is extended or adjusted under 35 U.S.C. 154(b) by 0 days.

(21) Appl. No.: 08/952,295

(22) PCT Filed: May 7, 1996

(86) PCT No.: PCT/EP96/01905

§ 371 Date: Nov. 10, 1997

§ 102(e) Date: Nov. 10, 1997

(87) PCT Pub. No.: WO96/35775

PCT Pub. Date: Nov. 14, 1996

(30) Foreign Application Priority Data

May 8, 1995 (CH) .................................................... 1317/95
Aug. 15, 1995 (CH) .................................................... 2337/95

(51) Int. Cl.$^7$ .................................................... C12N 1/20
(52) U.S. Cl. .................................... 435/253.3; 435/252.1; 435/280
(58) Field of Search ................................ 435/280, 252.1, 435/253.3

(56) References Cited

U.S. PATENT DOCUMENTS 4,080,259 * 3/1978 Boesten ............................. 435/252.1
4,880,737 * 11/1989 Kerkhoffs ............................. 435/106

FOREIGN PATENT DOCUMENTS 0 330 529 * 8/1989 (EP) .
0330529 * 8/1989 (EP) .
2 610 932 * 8/1988 (FR) .

OTHER PUBLICATIONS

Betz et al. J Gen Microbiol 75 (1). 1973 167–177.*

ATCC Catalogue of Bacteria, 1996, pp. 78–80.*

Clarke et al., J Gen Microbiol 71 (2). 1972 241–257.*

Bruce et al., Synth. Commun., 1995, 25 (17) 2673–2684.*

Chemical Abstracts, vol. 121, No. 25, Dec. 19, 1994, Abstract No. 301238, Massimo Falorni et al., "General and versatile approach to the synthesis of optically active 5–alkylpiperazine–2–carboxylic acids".*

Chemical Abstracts, vol. 123, No. 23, Dec. 4, 1995, Aabstract No. 313878, M. A. Bruce et al., Kinetic resolution of piperazinecarboxamide by leucine aminopeptidase. An application in the systhesis of the nucleoside transport blocker (–)–draflazine.*

* cited by examiner

Primary Examiner—Irene Marx
(74) Attorney, Agent, or Firm—Darby & Darby

(57) ABSTRACT

A biologically pure culture of microorganisms capable of converting RS-α-piperazinecarboxamides into the corresponding R-α-piperazinecarboxylic acid. R-α-piperazinecarboxamides is the only nitrogen source.

2 Claims, No Drawings

BIOTECHNICAL PRODUCTION PROCESS OF PIPERAZINE R-α-CARBOXYLIC ACIDS AND PIPERAZINE S-α-CARBOXYLIC ACID AMIDE

The invention relates to novel microorganisms which are capable of converting, in optionally substituted (RS)-α-piperazinecarboxamides, of the formula

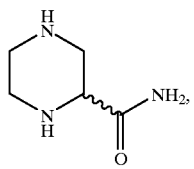

the optionally substituted R-α-piperazinecarboxamide into the corresponding optionally substituted R-α-piperazinecarboxylic acid, of the formula

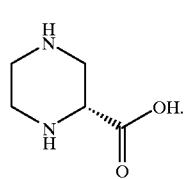

The microorganisms are capable of utilizing optionally substituted α-piperazinecarboxamides of the above formula I, in the form of their racemate or their optically active isomers, in particular R-α-piperazinecarboxamides, as the only nitrogen source. These microorganisms, or their cell-free enzymes, are employed in a novel process for the preparation of optionally substituted R-α-piperazinecarboxylic acids (formula II) and/or for the preparation of optionally substituted S-α-piperazinecarboxamides, of the formula

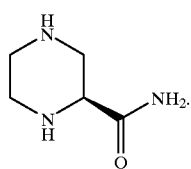

R-α-Piperazinecarboxylic acid, of the formula II, is an important intermediate for the preparation of (R)-2-carboxy-4-(3-phosphonopropyl)piperazine, which is a selective antagonist of N-methyl-D-aspartate (Synlett, 1996, 143–144).

A microbiological process for the preparation of R-α-piperazinecarboxylic acid has hitherto not been described in the literature.

It is an object of the present invention to provide a simple, technically feasible biotechnological process for the preparation of optically pure R-α-piperazinecarboxylic acids which simultaneously also allows S-α-piperazinecarboxamide to be isolated in high purity.

This object is achieved by the microorganisms according to patent claim 1 and by the process according to patent claim 3.

The microorganisms according to the invention can be isolated from soil samples, sludge or wastewater with the aid of customary microbiological techniques. According to the invention, these microorganisms are isolated in such a way that they are a) grown in the customary manner in a medium with an optionally substituted α-piperazinecarboxamide (formula I) in the form of its racemate or its optically active isomers as the only nitrogen source, preferably with an R-α-piperazinecarboxamide as the only nitrogen source, and with a suitable carbon source;

b) then, those which are stable and capable of converting, in (RS)-α-piperazinecarboxamides (formula I), the R-α-piperazinecarboxamide into the corresponding R-α-piperazinecarboxylic acid (formula II) are selected from the culture obtained by growing.

Accordingly, all microorganisms which specifically contain the R-piperazinecarboxamidases may be employed.

Examples of carbon sources which the microorganisms can utilize as growth substrates are sugars, sugar alcohols or carboxylic acids. Sugars which can be used are hexoses such as, for example, glucose, or pentoses. Carboxylic acids which can be used are di- or tricarboxylic acids or their salts such as, for example, citric acid or succinate. A sugar alcohol which may be used is, for example, glycerol. A sugar alcohol such as glycerol is preferably employed as the carbon source.

The selection and growth media which can be used are those conventionally used in expert circles, such as, for example, the mineral salt medium of Kulla et al. (Arch. Microbiol., 135, 1–7, 1983) or the medium described in Table 1. The medium described in Table 1 is preferably used.

It is expedient to induce the effective enzymes of the microorganisms during the growth and selection stage. Piperazinecarboxamide can be employed as the enzyme inductor.

The growth and selection stages are expediently carried out at a temperature of from 15 to 55° C., preferably from 20 to 45° C., and a pH of between pH 5 and pH 11, preferably between pH 6 and pH 10.

Preferred microorganisms with specific R-piperazinecarboxamidase activity are microorganisms of the genus Burkholderia, as well as their functionally equivalent variants and mutants. Especially preferred microorganisms are those of the genus Burkholderia, as deposited on Apr. 20, 1995 at the Deutschen Sammlung von Mikroorganismen und Zellkulturen GmbH, Mascheroder Weg 1b, D-38124 Braunschweig in accordance with the Budapest Treaty as DSM 9925, and their functionally equivalent variants and mutants.

Taxonomic characteristics of microorganisms of the genus Burkholderia (DSM 9925)

| | |
|---|---|
| Cell shape | rods |
| Width μm | 0.7–0.8 |
| Length μm | 1.5–3.5 |
| Gram reaction | − |
| Lysis by 3% KOH | + |
| Aminopeptidase (Cerny) | + |
| Spores | − |
| Oxidase | + |
| Catalase | + |
| Pigments | yellow |
| Growth anaerobic | − |
| PNPG | + |
| ADH | − |
| Urease | − |
| Hydrolysis of gelatine | − |

-continued

Substrate utilization

| | |
|---|---|
| Adipate | + |
| Citrate | little |
| Malate | + |
| Glucose | − |
| Adonitol | − |
| Mannitol | − |
| Suberate | + |
| Acetamide | + |
| 2,3-Butylene glycol | + |
| m-Hydroxybenzoate | + |
| α-Amylamine | + |
| Tryptamine | − |

Abbreviations:
PNPG: p-nitrophenyl-galactosidase
ADH: alcohol dehydrogenase

"Functionally equivalent variants and mutants" are to be understood as meaning microorganisms which have essentially the same characteristics and functions as the original microorganisms. Such variants and mutants can be formed accidentally, for example by UV irradiation.

The process according to the invention for the preparation of optionally substituted R-α-piperazinecarboxylic acid, of the formula

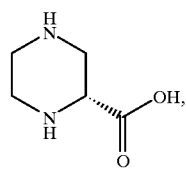

II and/or of optionally substituted S-α-piperazinecarboxamides, of the formula

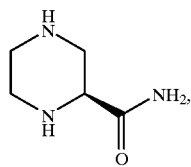

III is carried out in such a way that, in the optionally substituted (RS)-α-piperazinecarboxamide, of the formula

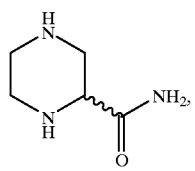

I the corresponding R-α-piperazinecarboxamide is converted into the corresponding R-α-piperazinecarboxylic acid by means of the specific microorganisms which have already been described or by means of cell-free enzymes from these microorganisms, and isolated, the biotransformation not only giving R-α-piperazinecarboxylic acid, but also S-α-piperazinecarboxamide, which, if appropriate, is isolated.

The starting materials, the (RS)-α-piperazinecarboxamides of the formula

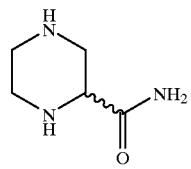

I which are optionally substituted can be obtained from the corresponding aromatic amides by hydrogenation methods conventionally used in the art.

The piperazinecarboxamides of the formula I which are employed can be substituted or unsubstituted. Representatives of substituted piperazinecarboxamides may be $C_1$–$C_4$-alkyl-substituted, such as, for example, 4-methylpiperazinecarboxamide, $H_2N$—$CH_2$-substituted, such as, for example, 4-aminomethylpiperazinecarboxamide or acyl-substituted, such as 4-acetylpiperazinecarboxamide. Piperazinecarboxamide or 4-methylpiperazinecarboxamide are preferably used.

The enzymes for the cell-free system can be obtained by rupturing the microorganisms by methods conventionally used in the art. Methods which can be used are, for example, ultrasonic, French press or lysozyme method. These cell-free enzymes can also be immobilized on a suitable support material.

Especially suitable for the process are the above-described specific microorganisms of the genus Burkholderia (DSM 9925), and their functionally equivalent variants and mutants.

After conventionally growing the microorganisms, biotransformation can be effected on dormant cells (non-growing cells which no longer require a carbon and energy source) or on growing cells.

Media which can be used for the process with dormant cells are those conventionally used in the art, such as, for example, the above-described mineral salt medium of Kulla et al., 1983 (ibid), low-molecular-weight phosphate buffers, HEPES buffers, or the medium described in Table 1. A medium which is used for the process with growing cells is normally one which comprises a carbon and nitrogen source, such as, for example, commercially available media or the medium of Table 1. The process is preferably carried out in the medium of Table 1.

Biotransformation is expediently effected with a single or continuous addition of such an amount of (RS)-α-piperazinecarboxamide that the concentration of (RS)-α-piperazinecarboxamide does not exceed 20% by weight, preferably 10% by weight.

The pH of the medium can be in a range of from pH to pH 11, preferably from pH 6 to pH 10.

Biotransformation is expediently effected at a temperature of from 15 to 55° C., preferably from 20 to 50° C.

After a customary reaction time of 1 to 100 hours, all of the R-α-piperazinecarboxamide of the formula I has been converted into R-α-piperazinecarboxylic acid, during which process S-α-piperazinecarboxamide is also obtained.

The R-α-piperazinecarboxylic acid and/or S-α-piperazinecarboxamide obtained in this manner can be isolated by customary work-up methods, such as, for example, by acidification, electrodialysis, chromatography or extraction. The S-α-piperazinecarboxamide which has been isolated can be hydrolysed chemically to give S-α-piperazinecarboxylic acid.

EXAMPLES

Example 1 a) Isolation of microorganisms which are capable of utilizing racemic piperazinecarboxamide as the only nitrogen source:

The medium used for isolating microorganisms which are capable of utilizing racemic piperazinecarboxamide as the only nitrogen source was the A-N medium, whose composition is shown in Table 1. 100 ml of this medium were introduced into a 300 ml Erlenmeyer flask and treated with various soil samples (2 g) from the works premises of LONZA AG in Visp, Switzerland. The flasks were incubated for 5 days at 30° C. without moving. Then, 1 ml of the A-N medium was used for inoculating a fresh flask with the same medium. Again, this flask was incubated under the same conditions. This enrichment cycle was repeated for a total of 5 times. Thereafter, the enrichment cultures were streaked out on agar medium (A-N medium with additionally 16 gl$^{-1}$ agar) to produce single colonies.

The microorganisms which had been isolated were tested in the following qualitative test system for stereoselective amidases. Single colonies were used for inoculating 100 ml of A-N medium in 300 ml Erlenmeyer flasks. These flasks were incubated for three days at 30° C. on a shaker, the cultures having grown fully after as little as one day. Thereupon, the cell-free culture supernatants were examined for piperazinecarboxylic acid and piperazinecarboxamide by means of thin-layer chromatography (silica gel, mobile phase: 11 parts ethanol, 6 parts CHCl$_3$, 6 parts NH$_4$OH (25%), detection by ninhydrin). Microorganisms which had reacted approximately half of the original amount of (RS)-piperazinecarboxamide were used for biochemical tests to ascertain which strains contained R-specific amidases.

b) Biochemical tests for identifying microorganisms with R-specific amidases:

To prepare protein crude extract, the cells were grown in 1 l of A-N medium at 30° C. and subsequently harvested and dried. 5 g of cells (fresh weight) were resuspended in 10 ml of 69 mM phosphate buffer, pH 7.0, and ruptured by means of a FRENCH® press. The crude extract was centrifuged for 2 hours at 40,000× g and then frozen in portions at −20° C. To determine the stereoselectivity, the hydrolysis rates of R-prolinamide and S-prolinamide were compared. To this end, the following enzyme test was used: assay volume 1 ml, containing 69 mM phosphate buffer, pH 7.0, 100–800 µg of protein crude extract, 2 mg of S- or R-prolinamide.HCl, incubation time 1–24 hours, incubation temperature 30° C., detection with ninhydrin after thin-layer chromatography (see above). The amidase of the strain termed DSM 9925 showed rapid hydrolysis of R-prolinamide. This strain was used for the preparation of optically active piperazinecarboxylic acid derivatives.

By altering the incubation temperature and the pH of the assay solution, it was found that the specific activity of the amidases was highest at a temperature of between 30 and 60° C. and a pH of 7–10.

TABLE 1

| A-N medium | |
|---|---|
| Composition | Concentration (mg/l) |
| (RS)-Piperazinamide | 2000 |
| Glycerol | 10,000 |
| Yeast extract | 500 |
| Na$_2$SO$_4$ | 100 |
| Na$_2$HPO$_4$ | 2000 |
| KH$_2$PO$_4$ | 1000 |
| NaCl | 3000 |
| MgCl$_2$x6H$_2$O | 400 |
| CaCl$_2$x2H$_2$O | 14.5 |
| FeCl$_3$x6H$_2$O | 0.8 |
| ZnSO$_4$x7H$_2$O | 100 x 10$^{-3}$ |

TABLE 1-continued

| A-N medium | |
|---|---|
| Composition | Concentration (mg/l) |
| MnCl$_2$x4H$_2$O | 90 x 10$^{-3}$ |
| H$_3$BO$_3$ | 300 x 10$^{-3}$ |
| CoCl$_2$x6H$_2$O | 200 x 10$^{-3}$ |
| CuCl$_2$x2H$_2$O | 10 x 10$^{-3}$ |
| NiCl$_2$x6H$_2$O | 20 x 10$^{-3}$ |
| NaMoO$_4$x2H$_2$O | 30 x 10$^{-3}$ |
| EDTA Na$_2$x2H$_2$O | 5 |
| FeSO$_4$x7H$_2$O | 2 |

Example 2

Preparation of R-piperazinecarboxylic Acid

The following conditions were chosen for the preparation of R-piperazinecarboxylic acid using the strains termed DSM 9925.

The cells were grown in A-N medium (Table 1) and then washed once with physiological saline. After they had been resuspended in 69 mM phosphate buffer, pH 8.0 and a cell density of 10 at OD$_{650}$ had been adjusted, 20 gl$^{-1}$ of (RS)-piperazinecarboxamide were added at a temperature of 47° C. The batch was then incubated for 18 hours (total volume: 200 ml, 31 mmol of (RS)-piperazinecarboxamide (4 g)). After the cells had been removed, the cell-free solution was concentrated under reduced pressure to 20 ml and then acidified with HCl to approximately pH 0, at which point the product precipitated. The acid which had been isolated was recrystallized in 0.1 M HCl and dried. 1.38 g (6.8 mmol) of R-piperazinecarboxylic acid were isolated as the dihydrochloride, which corresponds to a yield of 44 % based on the original amount of R-amide in the (RS)-piperazinecarboxamide. After derivatization with 2,3,4,6-tetra-O-acetyl-β-D-glucopyranosyl isothiocyanate, the ee value, i.e. the enantiomeric purity, measured by capillary electrophoresis was greater than 99%.

TABLE 2

| Conditions for capillary electrophoresis | |
|---|---|
| CE apparatus: | Hewlett-Packard HP $^{3D}$CE |
| Detector: | Hewlett-Packard diode array detector |
| Buffer: | 10 mM disodium hydrogen phosphate, 10 mM boric acid, 150 mM sodium dodecyl sulphate, pH 9.0 |
| Electrolyte: | 900 ml of buffer plus 100 ml of methanol |
| Capillary: | HP G1600-61211 |
| Electric field: | 20 kV |
| Current: | approx. 24–30 µA |
| Oven temperature: | 20° C. |
| Detector setting: | 210 nm (range 5 nm) |
| Migration time: | approx. 17.1 min. (S acid) approx. 17.7 min. (R acid) |

What is claimed is:

1. A biologically pure culture of Burkholderia strain DSM 9925 which converts a substituted or unsubstituted R-α- piperazinecarboxamide in a mixture of substituted or unsubstituted (RS)-α-piperazinecarboxamides of the formula

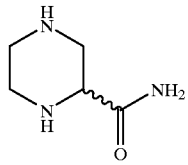

I into the corresponding substituted or unsubstituted R-α-piperazinecarboxylic acid of the formula

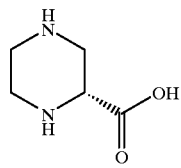

II wherein the substitution is selected from the group consisting of $C_1$–$C_1$ alkyl-, $H_2N$—$CH_2$— and acyl-.

2. The biologically pure culture of claim 1, wherein the substituted R-α-piperazinecarboxamide is selected from the group consisting of 4-methylpiperazinecarboxamide, 4-aminomethylpiperazinecarboxamide, 4-acetylpiperazinecarboxamide, and 4-methylpiperazinecarboxamide.

* * * * *